United States Patent [19]
Lafont et al.

[11] Patent Number: 5,957,975
[45] Date of Patent: Sep. 28, 1999

[54] STENT HAVING A PROGRAMMED PATTERN OF IN VIVO DEGRADATION

[75] Inventors: Antoine Lafont, Paris; Michel R. Vert, Casteinau-le-Lez, both of France; Fredrick Cornhill, Cleveland, Ohio; Suming Li, Casteinau-le-Lez; Henri L. Garreau, Saint-Mathieu-de-Treviers, both of France

[73] Assignees: The Cleveland Clinic Foundation, Cleveland, Ohio; The University Paris V, Faculte Necker, France; The Centre National de la Recherche Scientifique, France; The University of Montpellier I, France

[21] Appl. No.: 08/990,401

[22] Filed: Dec. 15, 1997

[51] Int. Cl.[6] ........................................................ A61F 2/04
[52] U.S. Cl. .................................................. 623/1; 603/12
[58] Field of Search ............................................ 623/1, 12

[56] References Cited

U.S. PATENT DOCUMENTS

| | | |
|---|---|---|
| 2,127,903 | 8/1938 | Bowen . |
| 3,657,744 | 4/1972 | Ersek . |
| 4,279,249 | 7/1981 | Vert et al. . |
| 4,655,711 | 4/1987 | Weissman . |

(List continued on next page.)

FOREIGN PATENT DOCUMENTS

| | | | |
|---|---|---|---|
| 0 578 998 A1 | 6/1993 | European Pat. Off. .......... | A61F 2/04 |
| 0 578 998 B1 | 6/1993 | European Pat. Off. .......... | A61F 2/04 |
| WO93/06792 | 10/1992 | WIPO . | |

OTHER PUBLICATIONS

"Restinosis After Experimental Angioplasty: Intimal, Medial, and Adventitial Changes Associated with Contrictive Remolding", by LaFont, et al., *Circulation Research*, vol. 76, No. 6, Jun. 1995, pp. 996–1002.

"Effect of Alpha–tocopherol on Restenosis after Angioplasty in a Model of Experimental Atherosclerosis", by LaFont, et al., *J. Clin. Invest.*, vol. 95, Mar. 1995, pp. 1018–1025.

"Evaluation of Long–Term Bioresorbability of Endoarterially Placed Poly–Lactic Acid Polymer in the New Zealand White Rabbit", LaFont, et al., *67th Scientific Sessions Abstract Form*, Nov. 14–17, 1994.

"Progressive and Prolonged Inflation Reduces Hyperplasia but Increases Chronic Constriction After Angioplasty in the Atherosclerotic Rabbit", LaFont, et al., *67th Scientific Sessions Abstract Form*, Nov. 14–17 1994.

*Primary Examiner*—David H. Willse
*Assistant Examiner*—Suzette J. Jackson
*Attorney, Agent, or Firm*—Calfee, Halter & Griswold LLP

[57] ABSTRACT

The present invention provides a biodegradable polymeric stent having a programmed pattern of in vivo degradation. When deployed, the stent comprises a substantially cylindrical element having two open ends and a plurality of regions circumferentially spaced around the cylindrical element and extending from one open end to the other open end of the cylindrical element. Each of the regions is configured to have a desired in vivo lifetime. One region is designed to have a shorter in vivo lifetime than the other region or regions so that when the stent is deployed within the lumen of a vessel of a patient, the cylindrical element breaks apart from one open end of the cylindrical element to the other open end of the cylindrical element within a predetermined period of time after the stent is deployed in the patient. In one preferred embodiment the stent is a formed from a biodegradable polymeric band. The band includes a head having a slot and a tongue having a catch mechanism. The cylindrical element is formed by inserting a portion of the tongue through the slot to provide a cylindrical element having a first reduced diameter configuration. Following deployment, the cylindrical element is in a second expanded diameter configuration wherein the distal catch mechanism engages the inner surface of the head and prevents radial collapse or recoil of the polymeric stent. In a second preferred embodiment, the stent is formed from a plurality of interconnected polymeric bands.

36 Claims, 3 Drawing Sheets

U.S. PATENT DOCUMENTS

| | | |
|---|---|---|
| 4,693,249 | 9/1987 | Schenck et al. . |
| 4,733,665 | 3/1988 | Palmaz . |
| 4,740,207 | 4/1988 | Kreamer . |
| 4,770,176 | 9/1988 | McGreevy et al. . |
| 4,776,337 | 10/1988 | Palmaz . |
| 4,795,458 | 1/1989 | Regan . |
| 4,870,966 | 10/1989 | Dellon et al. ............................... 623/1 |
| 4,878,906 | 11/1989 | Lindemann et al. . |
| 4,879,135 | 11/1989 | Greco et al. . |
| 4,955,377 | 9/1990 | Lennox et al. . |
| 4,969,896 | 11/1990 | Shors . |
| 5,007,926 | 4/1991 | Derbyshire . |
| 5,035,694 | 7/1991 | Kasprzyk et al. . |
| 5,059,211 | 10/1991 | Stack et al. . |
| 5,078,726 | 1/1992 | Kreamer . |
| 5,078,736 | 1/1992 | Behl . |
| 5,085,629 | 2/1992 | Goldberg et al. . |
| 5,092,841 | 3/1992 | Spears . |
| 5,116,318 | 5/1992 | Hillstead . |
| 5,133,732 | 7/1992 | Wiktor . |
| 5,135,536 | 8/1992 | Hillstead . |
| 5,139,480 | 8/1992 | Hickle et al. . |
| 5,147,385 | 9/1992 | Beck et al. . |
| 5,163,952 | 11/1992 | Froix . |
| 5,178,618 | 1/1993 | Kandarpa . |
| 5,190,540 | 3/1993 | Lee . |
| 5,192,307 | 3/1993 | Wall ............................................. 623/1 |
| 5,213,580 | 5/1993 | Slepian et al. . |
| 5,292,321 | 3/1994 | Lee . |
| 5,306,286 | 4/1994 | Stack et al. . |
| 5,419,760 | 5/1995 | Narciso, Jr. . |
| 5,421,955 | 6/1995 | Lau et al. . |
| 5,423,885 | 6/1995 | Williams . |
| 5,527,337 | 6/1996 | Stack et al. ............................. 606/198 |
| 5,551,954 | 9/1996 | Buscemi et al. . |
| 5,556,413 | 9/1996 | Lam ......................................... 606/198 |
| 5,618,299 | 4/1997 | Khosravi et al. ....................... 606/198 |
| 5,637,113 | 6/1997 | Tartaglia et al. ........................... 623/1 |
| 5,665,114 | 9/1997 | Weadock et al. ........................... 623/1 |
| 5,700,286 | 12/1997 | Tartaglia et al. ........................... 623/1 |
| 5,728,152 | 3/1998 | Mirsch, II et al. ........................ 623/1 |
| 5,769,883 | 6/1998 | Buscemi et al. ........................... 623/1 |
| 5,788,979 | 8/1998 | Alt et al. .................................. 424/426 |
| 5,865,723 | 2/1999 | Love .......................................... 623/1 |

STENT HAVING A PROGRAMMED PATTERN OF IN VIVO DEGRADATION

BACKGROUND OF THE INVENTION

The present invention relates to expandable, biodegradable stents. More particularly, the present invention relates to intravascular stents that have a programmed pattern of in vivo degradation and, thus, are useful for inhibiting the chronic restenosis that commonly occurs following percutaneous transluminal coronary angioplasty of atherosclerotic arteries.

Atherosclerosis is a disease in which vascular lesions or plaques consisting of cholesterol crystals, necrotic cells, lipid pools, excess fiber elements and calcium deposits accumulate on the interior walls of an individual's arteries. The presence of such plaques in the artery leads to thickening of the arterial wall and narrowing of the lumen. Eventually the enlargement of such plaques can lead to an occlusion of the lumen of the artery at the site of the lesion. One of the most successful procedures for treating atherosclerosis of the coronary arteries is percutaneous transluminal coronary angioplasty, hereinafter referred to as "PTC angioplasty". PTC angioplasty consists of introducing a deflated balloon into the lumen of the atherosclerotic artery, placing the balloon adjacent the site of the plaque or atherosclerotic lesion, inflating the balloon to a pressure of approximately 6 to 20 atmospheres thereby "cracking" the plaque and increasing the cross-sectional area of the lumen of the artery.

Unfortunately, the pressure that is exerted on the plaque during PTC angioplasty also traumatizes the artery. Accordingly, in 30–40% of the cases the vessel either gradually renarrows or recloses at the locus of the original stenotic lesion. This gradual renarrowing or reclosure, which is hereinafter referred to as "chronic restenosis," is a phenomenon that occurs almost exclusively during the first three to six months following angioplasty. Studies of the mechanism of chronic restenosis have shown that it is due in large part to a chronic constriction of the artery at the site of the barotraumatization, hereinafter referred to as the "retractile form of restenosis", and to a lesser extent to a proliferation of smooth muscle cells, hereinafter referred to as the "proliferative form of restenosis". Lafont et al. (1995) Restenosis After Experimental Angioplasty, Circulation Res. 76:996–1002.

A number of approaches for preventing restenosis are currently being used or tested. One approach involves the use of bioactive agents to prevent proliferation of the smooth muscle cells. To date, the use of bioactive agents alone has proven to be unsuccessful. Another approach employs a metallic stent which is deployed at the site of the stenotic lesion following PTC angioplasty. Typically, metallic stents are made in the form of a mesh-like network of linked wires and open spaces. Although metallic stents have the mechanical strength necessary to prevent the retractile form of restenosis, their presence in the artery can lead to biological problems including vasospasm, compliance mismatch, and even occlusion. Occasionally, technical difficulties, including distal migration and incomplete expansion, have also been observed with metallic stents. Moreover, there are inherent, significant risks from having a metal stent permanently implanted in the artery, including erosion of the vessel wall. In addition, the constant exposure of the stent to the blood can lead to thrombus formation within the blood vessel.

Metallic stents do not inhibit the proliferative form of restenosis. Indeed, implantation of the metallic stent induces neointimal proliferation. Such neointimal proliferation leads to the accumulation of new cells in the open spaces of the mesh-like metallic stents and on the inside surfaces thereof. This neointimal proliferation is one of the primary causes of the restenosis that occurs in the 30% of the patients who suffer from restenosis while the metallic stent is in place.

Finally, metallic stents prevent vascular remodeling. Vascular remodeling is a physiological process of the arterial wall that occurs as the atherosclerotic plaque begins to narrow the lumen of the vessel. When this occurs the artery senses the increased wall shear stress and tensile stress. In response to these stresses, the artery attempts to enlarge the lumen. Such enlargement is thought to be the result of expansion of the arterial wall through a process of cellular proliferation which results in increasing the luminal length (i.e. partial circumference) of the arterial wall. Glagou et al (1987) Compensatory Enlargement of Human Atherosclerotic Coronary Arteries, N. Eng. J. Med. 316:1371–1375. Although this process is not without limit, it can allow for relative reformation of a normal lumen cross-sectional area even with a 40% atherosclerotic stenosis of the arterial walls.

Stents made from biodegradable polymers have also been suggested for preventing restenosis. Although, generally an attractive alternative to metallic stents, testing in animals has shown that biodegradable stents still suffer from multiple complications, including distal migration of the entire stent or portions thereof and formation of an occlusive thrombus within the lumen of the stent. Frequently, such polymeric stents are formed from a mesh-like polymer which results in a stent having holes or open spaces that allow growth of tissue into and around the stent. As with the metallic stents, restenosis can result from the accumulation of proliferating smooth muscle cells on the inside surface of such polymeric stents.

Accordingly, it is desirable to have a new stent design that overcomes the disadvantages of the current stent designs. A stent that prevents retractile restenosis and that minimizes the restenosis that results from neointimal proliferation within a permanent stent is desirable. A stent that is fully degradable in vivo and that is designed such that portions of the stent are incorporated into the wall of the passageway, particularly an artery, during the time the stent is being degraded is desirable. A biodegradable stent that is designed to allow physiologic enlargement of the lumen of the blood vessel via expansive remodeling of the arterial wall during the first three to six months following PTC angioplasty is especially desirable.

SUMMARY OF THE INVENTION

The present invention provides a biodegradable polymeric stent designed to prevent chronic constriction and to allow physiologic enlargement of the lumen of a blood vessel at the site of the original stenotic lesion during the initial three to six months following deployment of the stent. The stent has a programmed pattern of in vivo degradation. When deployed, the stent comprises at least one substantially cylindrical element having two open ends and a plurality of regions circumferentially spaced around the cylindrical element and extending from one open end to the other open end of the cylindrical element. Each of the regions is configured or designed to have a desired in vivo lifetime. At least one of the regions is designed to have a shorter in vivo lifetime than the other region or regions. This means that the region having the shorter in vivo lifetime degrades sooner after deployment than the regions having a longer in vivo lifetime. Thus, when stents designed in accordance with the present invention are deployed within the lumen of a vessel of a patient, the cylindrical element acquires one or more fissures which extend from one open end of the cylindrical element to the other open end of the cylindrical element within a desired, predetermined period of time after the stent is deployed in the patient. It has been determined that such fragmentation within a predetermined period of time after deployment allows for enlargement of the lumen of the vessel via the process of arterial remodeling.

In one preferred embodiment the stent is a formed from a biodegradable polymeric band comprising a head having a slot and a tongue comprising a catch or locking mechanism proximate the longitudinal edge thereof. The cylindrical element which has an inner and outer surface is formed by inserting a portion of the tongue through the slot to provide a cylindrical element having a first reduced diameter configuration. Following deployment, the cylindrical element is in a second expanded diameter configuration wherein the distal catch mechanism engages the inner surface of the head and prevents radial collapse or recoil of the polymeric stent. In a second preferred embodiment, the stent is formed from a plurality of interconnected polymeric bands each of which comprises a head having a slot and a tongue comprising a catch mechanism proximate the longitudinal edge thereof.

The present invention also relates to a method of mounting the stents of the present invention on a balloon catheter. The method comprises heating the stent to temperature above the glass transition temperature of the polymer used to form the stent; positioning the stent on a deflated balloon mounted on a catheter; and compressing the stent to a reduced diameter configuration to secure the stent to the balloon. The present invention also relates to an assembly which comprises the stent of the present invention mounted on a balloon catheter.

The present invention also relates to a method of reducing the risk of chronic restenosis that can occur in an artery of a patient following PTC angioplasty. The method employs an expandable stent comprising at least one substantially cylindrical element comprising two ends and a plurality of regions circumferentially spaced around the cylindrical element and extending from one end to the other end of the substantially cylindrical element. The stent is formed from one or more bioresorbable polymers and is designed to acquire a fissure which extends from one end of the cylindrical element to the other end of the cylindrical element within a predetermined range of time after the stent is deployed in the patient. The method comprises the steps of mounting the stent in a first diameter configuration on a balloon catheter; delivering the balloon and stent to the locus of a stenotic lesion; heating the stent to a temperature above the glass transition temperature of the polymer used to form the stent for a time sufficient to make the stent more malleable; inflating the balloon to expand the stent to a second diameter configuration such that the stent contacts the walls of the blood vessel; and then deflating and withdrawing the balloon.

DETAILED DESCRIPTION OF THE INVENTION

Figure 1:
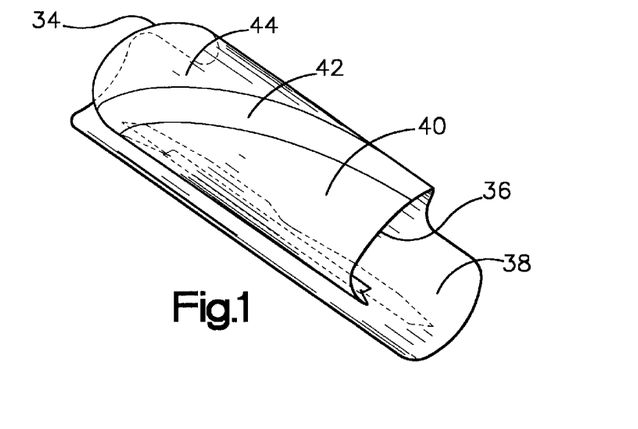
FIG. 1 is a perspective view of a stent formed in accordance with the present invention.

In accordance with the present invention, a biodegradable stent which allows for physiologic enlargement of the lumen of the vessel within which the stent is deployed is provided. When deployed, the stent comprises one or more substantially cylindrical elements that have a first open end and a second open end for allowing flow of a fluid, particularly blood, therethrough. Each cylindrical element may be a continuous cylinder. As used herein a continuous cylinder is one that has no free longitudinal edges. Polymeric stents that are in the form of a continuous cylinder are described in U.S. Pat. No. 5,306,286 to Stack. Preferably, each of the cylindrical elements is a discontinuous cylinder having two overlapping longitudinal edges as shown in FIG. 1. Each cylindrical element comprises at least two regions 42 and 44 circumferentially spaced around the cylindrical element and extending from lateral edge 34 defining the first open end of the cylindrical element to lateral edge 36 defining the second open end of the cylindrical element, as shown in FIG. 1. At least one of the regions has an in vivo lifetime, referred to hereinafter as the "first in vivo lifetime", that is shorter than the in vivo lifetime, referred to hereinafter as the "second in vivo lifetime" of the other regions. Preferably, the stent comprises a plurality of spaced apart regions having the first in vivo lifetime and a plurality of spaced apart regions having the second in vivo lifetime so that the stent breaks into a plurality of fragments within a predetermined time period, more preferably during the first in vivo lifetime, following deployment. For intravascular stents, particularly those used in coronary arteries, it is preferred that the first in vivo lifetime be from about 8 to 12 weeks, and that the second in vivo lifetime extend from about 16 to 52 weeks, more preferably from about 20 to 28 weeks.

The regions having the first in vivo lifetime can have any shape or even a plurality of shapes. As long as the regions having a first in vivo lifetime extend from one open end to the other open end of the cylindrical element, the pathway defined by such regions may be random or defined. Thus, the regions having a first in vivo lifetime may be in the form of a strip which extends along the longitudinal axis of the cylindrical element or which extends diagonally from one lateral edge to the other edge of the cylindrical element. Preferably, the width of each region having a first in vivo lifetime is less than the width of the regions having a second in vivo lifetime. Preferably, the overall surface area of the regions having a first in vivo life time is less than the surface area of the regions having a second in vivo lifetime.

The stents of the present invention are formed from a biodegradable, biocompatible, bioresorbable polymer, preferably a thermoplastic polymer. As used herein, a bioresorbable polymer is one whose degradative products are metabolized in vivo or excreted from the body via natural pathways. Such polymers include, for example, a polymer from the linear aliphatic polyester family, such as polylactic acid, polyglycolic acid or polycaprolactone and their associated copolymers. Polymers such as polyorthoester, polyanhydride, polydioxanone and polyhyroxybutyrate may also be employed. Preferably, the stent is formed from a thin layer of one or more amorphous, bioresorbable polymers, i.e., the polymers used to form the stent preferably are not crystalline. It is also preferred that the polymers used to form the stent do not generate crystalline residues upon degradation in vivo.

In one preferred embodiment, the stent comprises a polylactic acid stereocopolymer produced from L and DL lactides. The polymer is designated herein as "PLAX" where X represents the percentage of the L-lactic acid units in the mixture of monomers used to prepare the lactides. Preferably X is in the range of 10 to 90, more preferably 25 to 75. In another preferred embodiment, the stent comprises a poly-lactic acid, glycolic acid copolymer produced from L and DL lactides and glycolides. The polymer is designated herein as "PLAXGAY" where Y represents the percentage of glycolic acid units in the mixture of monomers used to prepare the copolymers. Preferably the copolymers do not contain glycolyl repeating units since such units are known to be more inflammatory than lactyl repeating units. Preferably, the polymers are prepared using Zn metal or Zn lactate as initiator. To ensure good initial mechanical properties of the stent, the molecular weight of the polymer in the region having the second in vivo lifetime is above 20,000 daltons, preferably 100,000 daltons. The polydispersity, $I=Mw/Mn$, must be below 2 and should not reflect the presence of low molecular weight oligomers smaller than 2,000 daltons as determined by size exclusion chromatography. Optionally, the polymeric layer used to make the stent may be impregnated with an anticoagulant agent, such as heparin, anti-oxidants, such as vitamin E, compounds that regulate cellular proliferation, or anti-inflammatory drugs, such as corticosteroids, to provide localized drug delivery. Such drugs are incorporated into the polymeric layer using techniques known in the art. For intravascular stents, it is preferred that the film have a thickness of from about 0.05 mm to 0.2 mm.

Stents having a plurality of regions with different in vivo lifetimes can be made in a variety of ways. Preferably, such stents are made by producing regions having a first in vivo lifetime, i.e. a shorter in vivo lifetime, in a polymeric layer having the predetermined second, or longer, in vivo lifetime. The regions having the first in vivo lifetime are produced by heating the respective regions of the polymeric layer having a second in vivo lifetime for a time and at a temperature sufficient to cause local partial degradation of the polymeric chains Such treatment, which can be accomplished using a piloted hot needle, laser beam, or flow of hot air, renders the polymer in the heated region more sensitive to hydrolytic degradation. Alternatively, the regions having a first in vivo lifetime may be produced in a polymeric layer having a second in vivo lifetime by incorporating a sufficient number of acidic ions into the respective regions of the polymeric layer. Preferably, the acidic ions are provided by compounds that are not soluble in blood.

Regions having a first in vivo lifetime can also be produced in a polymeric film having a second in vivo lifetime by exposure of the respective regions to beta radiation or gamma radiation for a sufficient time to induce partial cleavage of the polymeric chains within the respective regions. Provided the polymeric layer has a thickness of less than 0.3 mm, regions having a first in vivo lifetime can also be produced in a polymeric film having a second in vivo lifetime by reducing the thickness of the polymer in the respective region or forming holes therein. Regions having a first in vivo lifetime can also be produced in a polymeric film having a second in vivo lifetime by applying mechanical stress to the respective region. However, this latter process is difficult to control and, thus, is less preferred.

Another method for producing a polymeric layer in which one region or a plurality of spaced apart regions have a first in vivo lifetime and other regions have a second in vivo lifetime is to incorporate strips or fibers of a faster degrading bioresorbable polymer into a film made from a slower degrading polymer. For example, a mesh or a parallel array of fibers or strips of PGA or any other faster degrading bioresorbable polymer can be embedded into the respective regions of a polymeric film of PLA which may be designed to be slower degrading. Embedding can be achieved by inserting the mesh or fibers between two melted sheets of the slower degrading polymer. Provided the relative solubilities are compatible, the fibers or mesh can be placed in an organic solution of the slower degrading polymer and the desired polymeric film formed by evaporation of the organic solvent. One example of a method for embedding a mesh made from one polymer into a polymeric layer made from a second polymer is described in U.S. Pat. No. 4,279,249 issued to Vert et al. on Jul. 21, 1981, which is specifically incorporated herein by reference. A stent having the desired shape and orientation of regions is then formed from the polymeric layer by standard techniques such as stamping, employing a laser beam, or any other technique used in the art to tool a polymeric film.

First Embodiment

Figure 2A:
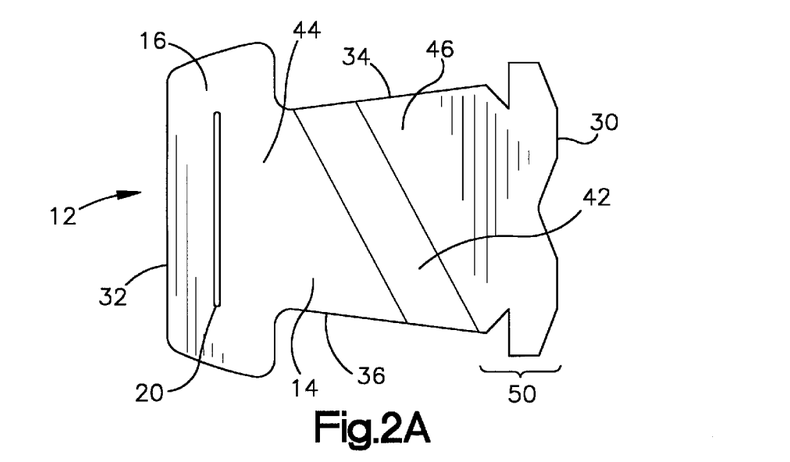
FIG. 2A is a plan view of one embodiment of a stent of the present invention prior to forming into a cylinder, where the stent comprises a single polymeric band.
Figure 2B:
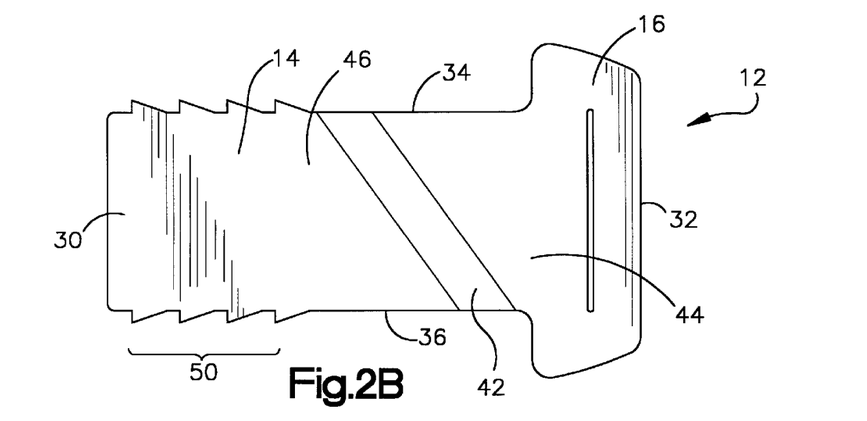
FIG. 2B is a plan view of another embodiment of a stent of the present invention prior to forming into a cylinder, where the stent comprises a single polymeric band

FIGS. 2A and B illustrate one preferred embodiment of a polymeric stent which generally incorporates features of the present invention. In this embodiment the stent comprises a bioresorbable polymeric band 12 with sufficient flexibility to form an annulus when the band is heated to a temperature above the glass transition temperature of the bioresorbable polymer and the band is wrapped around a balloon. Band 12 comprises a tongue 14 and a head 16. Band 12 further comprises a first longitudinal edge 30, a second longitudinal edge 32, a first lateral edge 34 and a second lateral edge 36. When formed into a cylinder, as depicted in FIG. 1, band 12 also has an inner surface 38 and an outer surface 40. Head 16 has a slot 20 configured to receive the portion of tongue 14 proximate first longitudinal edge 30 when the stent is formed into a cylinder. Band 12 contains two end regions 44 and 46 and a middle region 42, all of which extend lengthwise from first lateral edge 34 to second lateral edge 36 of band 12. End region 44, which is bordered by second longitudinal edge 32, contains slot 20. End region 46 contains the portion of tongue 14 which is proximate first longitudinal edge 30. Middle region 42 is disposed between and is adjacent to end region 44 and end region 46. In this embodiment, middle region 42 has a first in vivo lifetime, while end region 44 and end region 46 both have a second in vivo lifetime. The first in vivo lifetime of middle region 42 is shorter than the second in vivo life time of end region 44 and end region 46. In this manner, the stent is programmed to fragment or break apart at a predetermined time following deployment within a patient's vessel. Because middle region 42 has a shorter in vivo lifetime than end region 44 or end region 46, such break occurs within middle region 42 and at the end of the first in vivo lifetime.

A catch mechanism, shown generally as 50, for preventing recoil or collapse of the stent following deployment is present on tongue 14 proximate first longitudinal edge 30. Preferably, the catch mechanism comprises a widening at the distal portion of the tongue so that the distance between lateral edges 34 and 36 of band 12 in the distal portion of the tongue is greater than the length of the slot. More preferably, the catch mechanism is in the form of opposing projections on the distal portion of the tongue. Such projections from tip to base must have sufficient size and rigidity to lock the resulting discontinuous cylinder into its expanded size following deployment. Such projections must have sufficient size, resiliency, and orientation to permit passage of the projections through the slot when the tongue is inserted through the slot and again when the stent is expanded on the balloon.

In the embodiment depicted in FIG. 2A, the catch mechanism is in the form of a widening of tongue 14 from head 16 to longitudinal edge 30 and a pair of opposing notches present on lateral edges 34 and 36 of tongue 14. In the embodiment depicted in FIG. 2B, the catch mechanism is in the form of series of opposing teeth on lateral edges 34 and 36 and proximate first longitudinal edge 30.

Preferably, the width of slot 20 is only slightly larger than the thickness of tongue 14. Slot 20 can be cut into head 16 using stamping or any other method allowing polymer film tooling. Alternatively, slot 20 can be formed by bonding the edges of a separate thin band of polymer to the head proximate the lateral edges thereof.

Second Embodiment

Figure 3A:
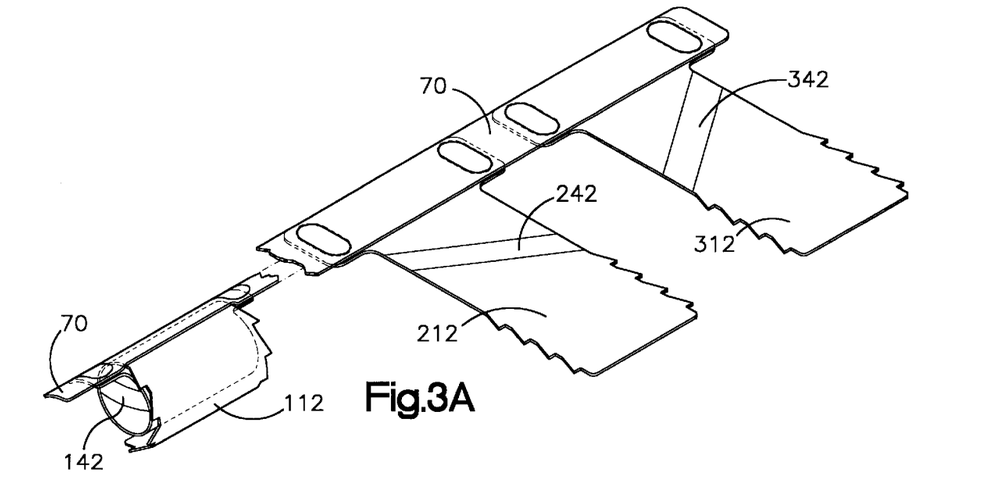
FIG. 3A is a view of one embodiment of a stent comprising a plurality of interconnected polymeric bands. The view depicts one of the bands being formed into a cylinder.
Figure 3B:
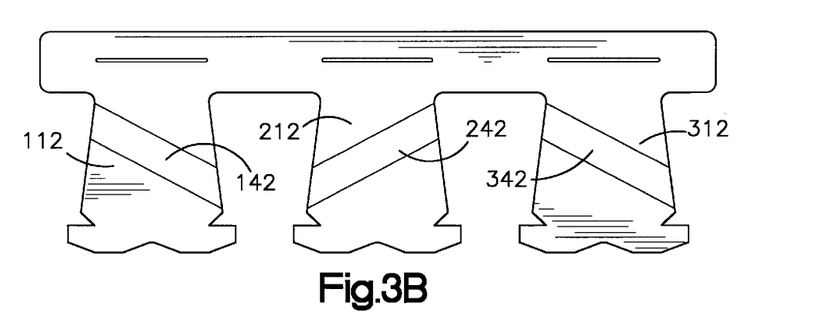
FIG. 3B is a plan view of another embodiment of the stent of the present invention prior to formation into a cylinder, where the stent comprises a plurality of interconnected polymeric bands.
Figure 4:
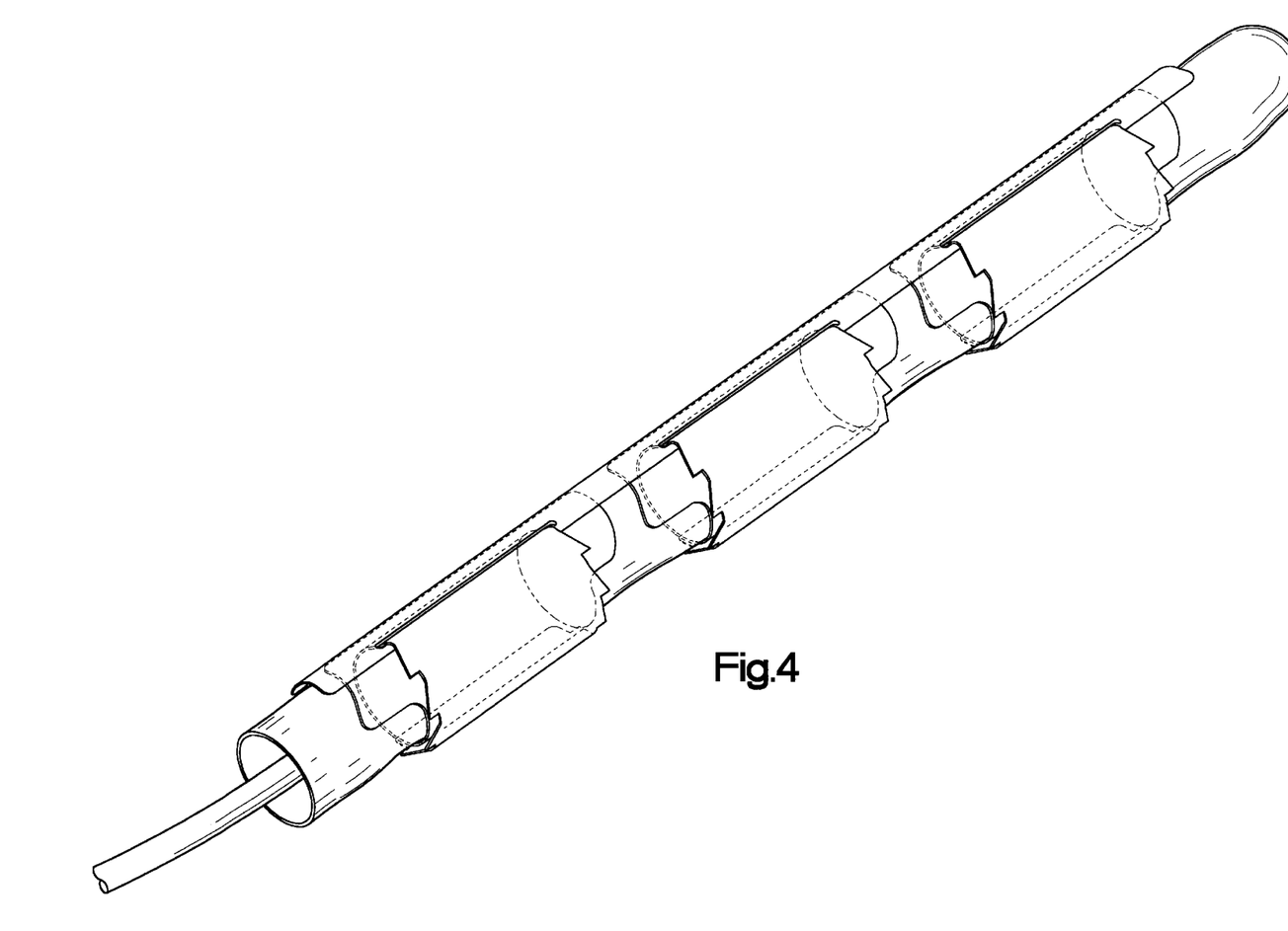
FIG. 4 is a perspective view of a stent formed in accordance with the present invention in its reduced diameter configuration and mounted on a balloon catheter.

In a second embodiment, the stent of the present invention comprises a plurality of bands as described in the first embodiment, where the bands are interconnected, preferably at the heads thereof. Turning now to FIGS. 3A and 3B which show two representative examples of this embodiment, the stent comprises three interconnected bands 112, 212 and 312. Bands 112, 212, and 312 are made from an expandable, bioresorbable, polymeric film having sufficient flexibility to form an annulus when wrapped around a balloon. Bands 112, 212, and 312 each comprise a middle region, 142, 242, and 342, respectively, which extends from one lateral edge to the other lateral edge of the band. Middle region 142, middle region 242, and middle region 342 all have a first in vivo lifetime which is shorter than the in vivo lifetime of the remaining regions of bands 112, 212, and 312, respectively. In this manner, the stent is programmed to fragment or break apart at a predetermined time following deployment of the stent within a patient's vessel. Such break occurs within regions 142, 242 and 342 at the end of the first in vivo lifetime. Each band comprises a head having a slot and a tongue comprising a catch mechanism for preventing recoil or collapse of the interconnected cylindrical elements that are formed when the stent is deployed.

The stent may further comprise one or a plurality of interconnecting elements which interconnect the head of each respective band. Preferably, the interconnecting elements are also formed from a bioresorbable polymer. The interconnecting elements and bands can be formed as a unitary structure as shown in FIG. 3A by stamping, cutting from a polymeric film employing a laser beam, or any other technique used in the art to tool a polymeric film. Alternatively, the interconnecting elements and band can be formed independently, as shown in FIG. 3B, and then connected by a suitable means such as by use of a bioresorbable, polymeric adhesive, local partial melting, or hot pressing. For example, each of the bands can be connected to a single backbone 70 as shown in FIG. 3A. In this latter case, the interconnecting elements and bands can be formed from the same or different polymers. The interconnecting elements or regions thereof may be designed to have an in vivo lifetime comparable to or less than the first in vivo lifetime. The interconnecting elements or regions thereof may be designed to have an in vivo lifetime comparable to or greater than the second in vivo lifetime. Finally the interconnecting elements or regions thereof may be designed to have an in vivo lifetime intermittent the first and second in vivo lifetimes.

This second embodiment is the preferred embodiment for use in tortuous pathways such as coronary arteries. This second embodiment is also the more preferred embodiment when the region to be stented is relatively long.

Assembly

The stents of the first and second embodiment are assembled into a delivery system in the same manner. Prior to positioning on a balloon, the distal region of the tongue of each band is inserted into its corresponding slot to form a cylinder. The tongue is inserted to a sufficient distance such that the catch mechanism on the lateral edges thereof passes through the slot. The stent is then heated to a temperature above the glass transition temperature of the polymer used to form the stent. The stent is heated for a time sufficient to render the stent more malleable. For bands prepared from PLA, a temperature of from about 50° to 60° C. is preferred. Preferably, the tongue is inserted into the slot so that the first longitudinal edge of each resulting discontinuous cylindrical element is in contact with the outside surface thereof. The region of the tongue lying on the outside of the cylinder is then wrapped around the cylinder and the cylinder compressed into a first diameter configuration, preferably while it is positioned on a balloon mounted on a catheter. The stent is then cooled to room temperature. Such procedure gives the polymeric stent a first memory of this reduced diameter configuration which aids in keeping the stent in place on the balloon. Optionally, a thin membrane may be applied to the entire outside surface of the stent to ensure that each of the resulting cylinders stays in its first diameter configuration and positioned on the balloon during movement of the stent through vessel to the site of the stenotic lesion. The system, comprising stent, catheter, and balloon, and, optionally membrane, are then sterilized by standard procedures such as, for example, exposure to vaporized hydrogen peroxide, gamma radiation, electron beam, or, preferably, ethylene oxide. Assembly in a sterile atmosphere is preferred. The sterile assembly is then ready for introduction into a vessel.

Delivery and Deployment

For delivery to the desired site, an assembly comprising the stent of the present invention mounted on an expandable catheter, preferably a balloon catheter, is percutaneously introduced into a vessel. Optionally, if the stent is provided with a mechanism such as for example a membrane which keeps the stent secured to the balloon catheter, the stent may be heated for a time and temperature sufficient to provide greater malleability to the stent prior to introduction into the vessel. The catheter is advanced with the aid of a guidewire and under fluoroscopic control to the site of the stenotic lesion. The balloon and stent are then disposed within the constricted portion of the vessel.

Figure 5A:
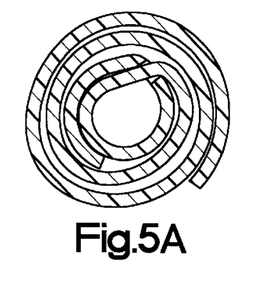
FIGS. 5A and 5B are cross-sectional views of the stents shown in FIG. 2, showing the stent in a first reduced diameter configuration and a second expanded diameter configuration, respectively.
Figure 5B:
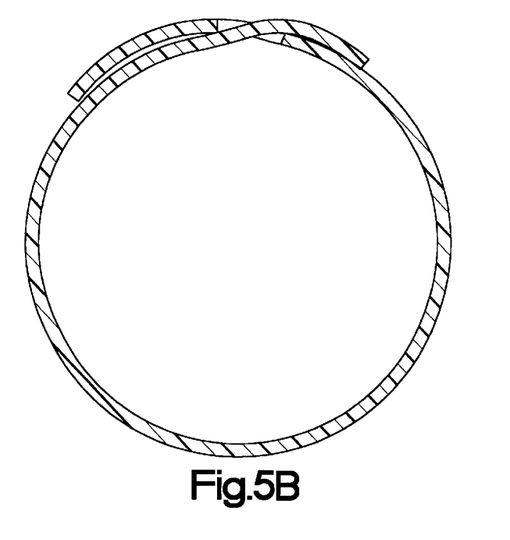

After the stent and balloon are delivered to the locus of the stenotic lesion, the optional membrane is removed. The balloon is first heated and then inflated to expand the stent from the first configuration which has a reduced diameter to a second configuration having an enlarged diameter greater than or equal to the interior of the passageway wall so that the stent abuts the wall of the vessel. Thus the cylindrical elements of the stent have a first configuration with a reduced diameter prior to deployment, as represented in FIG. 5A and a second configuration with an expanded diameter following deployment, as represented in FIG. 5B. The diameters of the cylindrical element depend on the size of the passageway into which the stent is introduced. Typically, for coronary arteries, the reduced diameter of the cylindrical element prior to deployment is from about 0.5 to about 1 mm and expanded diameter after deployment is from about 3 mm to about 5 mm.

Fracturing of the plaque and deployment of the stent may be done concurrently. In such cases, the balloon is inflated to a pressure of about 8 to 12 atmospheres to crack the plaque and expand the stent. Alternatively, the vessel may be pre-dilated using PTC angioplasty without the stent. Thereafter, the stent is introduced into the desired site on a separate expandable catheter, preferably a balloon catheter.

After the stent is positioned at the site but before expansion, the stent is heated to a temperature greater than the glass transition temperature of the polymers used to form the stent. Heating is for less than 30 seconds, preferably less than 10 seconds. Heating of the stent prior to expansion thereof makes the stent more malleable and avoids development of unprogrammed ruptures in the stent. Heating prior to expansion also permits the tongue to go through the slot without breaking, thereby avoiding damage to the locking mechanism. Such heating also gives the polymeric stent a second memory of the second expanded diameter configuration. Such second memory aids in preventing radial collapse of the stent before the time period defined by the first in vivo lifetime. Suitable methods for heating the stent during or after expansion include, for example, use of a laser balloon or a radiofrequency balloon.

Once expanded, the stents of the present invention are retained in position by friction with the inner wall of the vessel and the second memory imparted by heating the stent prior to expansion. Radial collapse is prevented primarily by engagement of the catch mechanism on the tongue with the inner surface of the head. Eventually, when the regions having the first in vivo life time are degraded, the stent is fragmented and the regions having a second in vivo lifetime are entrapped within the arterial intima.

It has been found that stents designed in accordance with the present invention, i.e. stents programmed to fragment in a predetermined manner and at a desired time following deployment in a patient, allow for acute structural support of the artery and thus prevents the retractile restenosis that normally occurs within three months of deployment of the stent at the locus of the stenotic lesion. It has also been discovered that stents designed in accordance with the present invention allow arteries damaged by PTC angioplasty to restructure or remodel themselves and, thus, maintain a normal lumen cross-sectional area even in the presence of intimal smooth muscle cell proliferation. It has also been found that when stents designed in accordance with the present invention are deployed at a site barotraumatized by angioplasty, the regions having a longer in vivo lifetime are incorporated into the wall of the artery, thereby preventing the distal migration of such segments and the likelihood of embolization.

The following examples are for purposes of illustration only and are not intended to limit the scope of the invention as defined in the claims which are appended hereto.

EXAMPLE 1

A film of PLA 92 was used to prepare a stent comprising a single substantially cylindrical element comprising regions with different in vivo lifetimes. PLA 92 was synthesized from a mixture of 84/16 L-lactide/DL-lactide (PLA 92). The monomer was introduced into a reactor with 0.05% of zinc powder as primer. The polymerization was done at 145° C. under vacuum for 8 days. The resulting polymers were purified by dissolution and precipitation using acetone or chloroform as solvent and ethanol as nonsolvent. The size exclusion chromatography was done using a WATERS apparatus, equipped with two columns of $\mu$-styragel and refractometric detector, the mobile phase being dioxane. The DSC thermograms were taken using a Dupont calorimeter, Series 99, equipped with a cell, the temperature increase being 10° C./min.

The polymer was formed into a film of about 0.1 to 0.2 mm thickness by means of compression molding. Then a stent having the form depicted in FIG. 2B was made from the film by stamping with a metal punch. In order to have a stent of three different expanded diameter configurations, three pairs of opposing teeth were placed along the lateral edges of the tongue. The overall length was 15 mm, the height of the cylinder being 9 mm at the level of the tongue and 15 mm at the level of the head. The slot was 8.5 mm long, the teeth measured 0.1 mm from base to tip. The total length of the tongue was 13 mm, the length of the body 7 mm, the combined body and tongue measured 20 mm. The bulkiness was reduced by diminishing the thickness of the polymer film used to around 0.15 mm. The tongue was inserted into the slot and the stent was then placed in a water bath at temperature of 50° to 60° C. and rolled up into a cylinder having a first reduced diameter configuration. The rolling was done around a metal guide of 0.014 inches. The guide was then introduced into the lumen of a balloon catheter and the stent was then slid from the guide and advanced over the deflated balloon. The entire assembly was placed in the bath at a temperature of between 50° to 60° C. and the stent was firmly secured to the balloon by tightly squeezing the cylinder around the balloon. It was shown that the mechanical stresses applied to the stent during assembly generated visually detectable defects in the stent. It is believed that such defects resulted in the formation in the stent of regions having a shorter in vivo lifetime.

EXAMPLE 2

A stent having the form shown in FIG. 2A was cut from a polymeric layer of PLA50 and assembled as described in example 1. The PLA 50 film was made from mass polymerization of DL-lactide and compression molding.

The stents made as described in example 1 and 2 were deployed into the aortas of three different groups of rabbits for evaluation. The deployment procedure consisted of three inflations at 8 atmospheres for one minute, using a balloon of 3.5 mm. After every deployment procedure, an angiogram was performed to evaluate the immediate result (good result, spasm or occlusion). At 15, 30, 90, and 180 days a group of surviving animals were sacrificed. Prior to sacrifice, the animals were examined by angiography to detect any stenosis occurring at the stent. Immediately after angiographic examination and before killing the animal, an abdominal laparatomy was performed to enable macroscopic examination of the aorta in vivo. The aortic segment containing the stent was removed after fixation in vivo, examined, and then prepared for histology and/or biochemical evaluation.

In those cases where there was satisfactory deployment and no rolling up of the stent due to failure of the locking mechanism or premature fracture, the results of these evaluations indicated that the stent remained patent in the long term. There was limited thrombosis with organization of the thrombus and its subsequent endothelialization. In those cases which were successful, the arterial wall presented no reaction of neointimal hyperplasia and/or no inflammatory phenomenon in the area of the media. When the stent was deployed with success, there was no intact prosthesis at the end of the six month period. In two cases there was an almost complete degradation of the prosthesis, leaving behind only residues inside a neointima of moderate size and a lumen without narrowing. These results demonstrated that the stents had been able to degrade. These results also indicated that the stents had allowed the artery to adjust its diameter. It is believed that the restructuring by enlargement occurred in large part due to a fragmentation of the stent at a suitable time after deployment. Thus, during the first 3 months after angioplasty, the stents of the present invention resisted constrictive restructuring, like a metal stent. Between 3 and 6 months after deployment, a fragmentation of the stent by differentiated bioresorption allowed remodeling of the arterial wall and enlargement of the lumen, which was observed through histology and angiography. This second function cannot be fulfilled by a metal stent.

In addition to coronary arteries, the present stent may be used in other arteries such as for example, femeroiliac arteries, the carotid artery, vertebro-basilar arteries, as well as in the interior of other hollow passageways such as for example veins, ureters, urethrae, bronchi, biliary and pancreatic duct systems, the gut, eye ducts, and spermatic and fallopian tubes. Accordingly, the dimensions and degradation rates set forth for the above embodiments which are described as being suitable for use in coronary arteries are not intended to and should not limit the stent to only those dimensions and degradation rates.

While the invention has been described to some degree of particularity, various adaptations and modifications can be made without departing from the scope of the invention as defined in the appended claims.

What is claimed is:

1. A biodegradable polymeric stent having a programmed pattern of in vivo degradation, said stent comprising:
   a substantially cylindrical element having two open ends and comprising a plurality of regions circumferentially spaced around the cylindrical element, each region of said plurality of regions extending from one open end to the other open end of said cylindrical element, wherein at least two adjacent regions of said plurality of regions are configured to have different predetermined in vivo lifetimes;
   a first region of said plurality of regions having a first in vivo lifetime;
   a second region of said plurality of regions having a second in vivo lifetime, said second region being juxtaposed to said first region and;
      wherein the first in vivo lifetime of said first region is shorter than the second in vivo lifetime of said second region such that said cylindrical element selectively breaks apart within said first region within a predetermined period of time following deployment of the stent in a vessel of a patient.

2. The stent of claim 1 wherein the stent comprises a plurality of spaced apart first regions having a first in vivo lifetime and a plurality of spaced apart second regions having a second in vivo lifetime.

3. The stent of claim 1 wherein the stent comprises a plurality of said substantially cylindrical elements, said plurality of said substantially cylindrical elements being interconnected.

4. The stent of claim 1 wherein the stent is an intravascular stent; wherein the first in vivo lifetime of said first region is from about 8 to about 12 weeks; and wherein the second in vivo lifetime of said second region is from about 16 to about 52 weeks.

5. The stent of claim 3 wherein the stent is an intravascular stent; wherein the first in vivo lifetime of said first region is from about 8 to about 12 weeks; and wherein the second in vivo lifetime of said second region is from about 16 to about 52 weeks.

6. The stent of claim 3 wherein the plurality of cylindrical elements are interconnected by an interconnecting element, and wherein said interconnecting element or a region thereof is configured to have an in vivo lifetime substantially the same as or less than the first in vivo lifetime of said first region.

7. The stent of claim 3 and wherein the plurality of cylindrical elements are interconnected by an interconnecting element, and wherein said interconnecting element or a region thereof is configured to have an in vivo lifetime substantially the same as or greater than the second in vivo lifetime of said second region.

8. The stent of claim 3 wherein the plurality of cylindrical elements are interconnected by an interconnecting element, and wherein said interconnecting element or a region thereof is configured to have an in vivo lifetime intermittent the first in vivo lifetime of said first region and the second in vivo lifetime of said second region.

9. The stent of claim 1 wherein the stent is formed from one or more amorphous polymers that are free from crystalline residues upon degradation in vivo.

10. The stent of claim 1 wherein the stent is formed from a polylactic acid polymer produced from L and DL-lactides, and wherein the percentage of L-lactic acid units in the mixture of monomers used to prepare said lactides ranges from about 10 to about 90%.

11. The stent of claim 10 wherein the percentage of L-lactic acid units in the mixture of monomers used to prepare said lactides ranges from about 25 to about 75%.

12. The stent of claim 3 wherein the stent is formed from one or more amorphous polymers that are free from crystalline residues upon degradation in vivo.

13. The stent of claim 3 wherein the stent is formed from a polylactic acid polymer produced from L and DL-lactides, and wherein the percentage of L-lactic acid units in the mixture of monomers used to prepare said lactides ranges from about 10 to about 90%.

14. The stent of claim 13 wherein the percentage of L-lactic acid units in the mixture of monomers used to prepare said lactides ranges from about 25 to about 75%.

15. The stent of claim 13 wherein the stent is heated to a temperature above the glass transition temperature of the polymer prior to expansion of said stent to provide said stent with a memory of an expanded diameter configuration.

16. The stent of claim 1 wherein the stent is formed from a polylactic acid and glycolic acid copolymer produced from L-lactides, DL-lactides and glycides.

17. The stent of claim 3 wherein the stent is formed from a polylactic acid and glycolic acid copolymer produced from L-lactides, DL-lactides and glycides.

18. The stent of claim 1 wherein said substantially cylindrical element breaks apart within said first in vivo lifetime to allow remodeling of the vessel.

19. A biodegradable stent for use in a vessel of a patient, said stent comprising:
   a polymeric band having two longitudinal edges that overlap when said stent is formed into a cylinder, two lateral edges defining two open ends when said stent is formed into a cylinder, and an inner and outer surface when said stent is formed into a cylinder; said band comprising:

a head and a tongue;
said head having a slot for receiving a distal portion of said tongue when said stent is formed into a cylinder;
said distal portion of said tongue comprising a catch mechanism for contacting the inner surface of said stent and preventing radial collapse of said stent following deployment of said stent in the vessel
wherein said polymeric band comprises a plurality of regions spaced across the band;
each region of said plurality of regions extending from one lateral edge to the other lateral edge of said polymeric band, wherein at least two adjacent regions of said plurality of regions are configured to have different predetermined in vivo lifetimes;
a first region of said plurality of regions having a first in vivo lifetime;
a second region of said plurality of regions having a second in vivo lifetime;
wherein the first in vivo lifetime of said first region is shorter than the second in vivo lifetime of said second region such that said polymeric band breaks apart within said first region following deployment of the stent in a vessel of a patient.

20. The stent of claim 19 wherein said stent comprises a plurality of polymeric bands, said plurality of polymeric bands being interconnected, each of said bands comprising a head having a slot and a tongue having a catch mechanism.

21. The stent of claim 19 wherein said catch mechanism comprises opposing projections on the lateral edges of the tongue.

22. The stent of claim 20 wherein the catch mechanism on each tongue comprises opposing projections of the lateral edges of the tongue.

23. The stent of claim 19 wherein the stent is formed from one or more amorphous polymers that are free from crystalline residues upon degradation in vivo.

24. The stent of claim 19 wherein the stent is formed from a poly-lactic acid polymer produced from L and DL-lactides, and wherein the percentage of L-lactic acid units in the mixture of monomers used to prepare said lactides ranges from about 10 to about 90%.

25. The stent of claim 24 wherein the percentage of L-lactic acid units in the mixture of monomers used to prepare said lactides ranges from about 25 to about 75%.

26. The stent of claim 20 wherein the stent is formed from one or more amorphous polymers that do not generate crystalline residues upon degradation in vivo.

27. The stent of claim 19 wherein the stent is formed from a poly-lactic acid polymer produced from L and DL-lactides, and wherein the percentage of L-lactic acid units in the mixture of monomers used to prepare said lactides ranges from about 10 to about 90%.

28. The stent of claim 27 wherein the percentage of L-lactic acid units in the mixture of monomers used to prepare said lactides ranges from about 25 to about 75%.

29. The stent of claim 19 wherein the stent is formed from a poly-lactic acid and glycolic acid copolymer produced from L-lactides, DL-lactides and glycides.

30. The stent of claim 1 wherein the width of said first region is less than the width of said second region.

31. The stent of claim 2 wherein the width of each of said first region is less than the width of each of said second region.

32. The stent of claim 1 wherein the overall surface area of said first region is less than the overall surface area of said second region.

33. The stent of claim 2 wherein each of said first regions has an overall surface area that is less than the overall surface area of each of said second regions.

34. The stent of claim 1 wherein said first region comprises polymeric chains that are shorter than the polymeric chains in said second region.

35. The stent of claim 1 wherein said first region comprises acidic ions.

36. The stent of claim 1 wherein said second region comprises a first bioresorbable polymer having a first in vivo degradation rate and wherein said first region comprises a second bioresorbable polymer having a second in vivo degradation rate; said second in vivo degradation rate of said second polymer being faster than said first in vivo degradation rate of said first polymer.

* * * * *